United States Patent
Gigon

(10) Patent No.: US 10,201,334 B2
(45) Date of Patent: Feb. 12, 2019

(54) COUPLING DEVICE BETWEEN THE DRIVE SHAFT OF A SURGICAL INSTRUMENT AND A TOOL

(75) Inventor: David Gigon, Le Noirmont (CH)

(73) Assignee: BIEN-AIR HOLDING S.A., Bienne (CH)

( * ) Notice: Subject to any disclaimer, the term of this patent is extended or adjusted under 35 U.S.C. 154(b) by 361 days.

(21) Appl. No.: 12/912,664

(22) Filed: Oct. 26, 2010

(65) Prior Publication Data

US 2011/0098688 A1    Apr. 28, 2011

(30) Foreign Application Priority Data

Oct. 28, 2009   (EP) ..................................... 09174374

(51) Int. Cl.
| | |
|---|---|
| A61B 17/00 | (2006.01) |
| A61B 17/32 | (2006.01) |
| A61B 17/16 | (2006.01) |
| A61B 17/14 | (2006.01) |

(52) U.S. Cl.
CPC .......... *A61B 17/00* (2013.01); *A61B 17/144* (2016.11); *A61B 17/162* (2013.01); *A61B 17/1688* (2013.01); *A61B 17/32002* (2013.01); *A61B 17/1646* (2013.01); *A61B 2217/007* (2013.01)

(58) Field of Classification Search
USPC ........................................ 606/1, 79, 80, 180
See application file for complete search history.

(56) References Cited

U.S. PATENT DOCUMENTS

| | | | | |
|---|---|---|---|---|
| 3,936,940 | A | * | 2/1976 | Loge .................. A61C 1/18 433/126 |
| 4,020,555 | A | * | 5/1977 | Hedrick ................ A61B 17/14 279/89 |
| 4,063,557 | A | * | 12/1977 | Wuchinich et al. ............ 604/22 |
| 4,108,182 | A | * | 8/1978 | Hartman ............ A61F 9/00763 30/133 |
| 4,246,902 | A | * | 1/1981 | Martinez ............ A61F 9/00763 604/22 |
| 4,314,560 | A | * | 2/1982 | Helfgott et al. ............. 606/171 |
| 4,975,056 | A |  | 12/1990 | Eibofner |
| 5,340,129 | A | * | 8/1994 | Wright .................. A61B 17/14 279/90 |
| 5,364,395 | A | * | 11/1994 | West, Jr. ........................ 606/46 |

(Continued)

FOREIGN PATENT DOCUMENTS

| | | |
|---|---|---|
| EP | 0 517 529 A2 | 12/1992 |
| EP | 1 623 677 A1 | 2/2006 |

(Continued)

OTHER PUBLICATIONS

The American Heritage(R) Dictionary of the English Language, definition of shank, 2000.*

(Continued)

*Primary Examiner* — Carl H Layno
*Assistant Examiner* — Manolis Pahakis
(74) *Attorney, Agent, or Firm* — Oblon, McClelland, Maier & Neustadt, L.L.P.

(57) ABSTRACT

Coupling device between a drive shaft of a surgical instrument and a tool, characterized in that the coupling device includes a fluid feed element fed from outside the coupling device and communicating with a channel arranged in the tool and which emerges at a location along the length of the tool.

19 Claims, 4 Drawing Sheets

(56) References Cited

U.S. PATENT DOCUMENTS

| | | | | |
|---|---|---|---|---|
| 5,487,747 | A * | 1/1996 | Stagmann | A61F 9/00763 604/22 |
| 5,575,071 | A * | 11/1996 | Phillips | B23D 51/10 279/71 |
| 5,741,272 | A * | 4/1998 | Kuhne | 606/128 |
| 5,792,167 | A * | 8/1998 | Kablik et al. | 606/180 |
| 5,807,401 | A * | 9/1998 | Grieshaber | A61F 9/00763 604/22 |
| 5,871,493 | A | 2/1999 | Sjostrom et al. | |
| 5,989,257 | A | 2/1999 | Tidwell et al. | |
| 5,916,231 | A * | 6/1999 | Bays | 606/180 |
| 5,922,003 | A * | 7/1999 | Anctil et al. | 606/170 |
| 6,065,966 | A | 5/2000 | Loehn et al. | |
| 6,213,971 | B1 * | 4/2001 | Poole | 604/35 |
| 6,214,017 | B1 * | 4/2001 | Stoddard | A61B 17/320068 606/128 |
| 6,595,996 | B2 * | 7/2003 | Dinger et al. | 606/84 |
| 6,638,290 | B2 * | 10/2003 | Pascaloff | A61B 17/14 279/48 |
| 6,715,211 | B1 * | 4/2004 | Chi | B23D 51/10 30/329 |
| 6,725,548 | B1 * | 4/2004 | Kramer | B23D 51/10 279/75 |
| 2005/0261693 | A1 * | 11/2005 | Miller et al. | 606/80 |
| 2006/0025792 | A1 * | 2/2006 | Gibson et al. | 606/170 |
| 2006/0121413 | A1 * | 6/2006 | Turner | A61C 1/05 433/114 |
| 2007/0100336 | A1 * | 5/2007 | McFarlin et al. | 606/45 |
| 2009/0326540 | A1 * | 12/2009 | Estes | A61B 17/14 606/82 |
| 2011/0202023 | A1 * | 8/2011 | Stanton et al. | 604/319 |

FOREIGN PATENT DOCUMENTS

| | | |
|---|---|---|
| EP | 1 974 680 A1 | 10/2008 |
| FR | 2 635 676 A1 | 3/1990 |

OTHER PUBLICATIONS

Bien Air, Products, Dec. 1, 2007 (Retrieved with the Wayback machine for links: http://www.bienair.com/surgery_products_b.asp?familly=189 and http://www.bienair.com/surgery_products_b.asp?familly=204).*

European Search Report issued in corresponding application No. 09 17 4374, completed May 5, 2010.

Office Action issued in corresponding European application 09174374.0 dated Apr. 2, 2013 (no translation available; submitted for certification).

Random House Webster's College Dictionary 185, 954 and 1483 (1991).

www.bienairsurgery.com : "Powered Microsaw Rhinoplasty The Future of Aesthetic Nose Surgery", Swiss Made, pp. 1-39, REF 2400223G, Jun. 2015 EN.

* cited by examiner

COUPLING DEVICE BETWEEN THE DRIVE SHAFT OF A SURGICAL INSTRUMENT AND A TOOL

This application claims priority from European Patent Application No. 09174374.0 filed Oct. 28, 2009, the entire disclosure of which is incorporated herein by reference.

FIELD OF THE INVENTION

The present invention concerns a coupling device between the drive shaft of a surgical instrument and a tool. More specifically, the present invention concerns a coupling device between a motorised surgical instrument and a rhinoplasty tool.

BACKGROUND OF THE INVENTION

Rhinoplasty is a branch of cosmetic surgery that aims to redesign the profile of a patient's nose. One particular case is correction by bone ablation of the bump on the ridge of the nose that is more pronounced in some people than in others. In order to perform this ablation, the surgeon uses motorised handpieces that impart specific back and forth movements to saw, file or plane type tools. An example of this type of handpiece is illustrated in FIG. 1 annexed to this Patent Application. Designated as a whole by the general reference number 1, the handpiece includes a generally cylindrical body 2 inside which are housed an electric motor and a shaft driven by the motor (not visible in the drawing). A coupling bushing 4 enables a tool 6, such as a saw blade, to be removably mounted on the drive shaft. The surgeon holds handpiece 2 in his hand by body 2 thereof. For this purpose, a grooved surface 8 can be provided, which will define a non-slip gripping area.

The success of the operation depends partly upon the quality of the handpiece and the tools used. It also partly depends upon the irrigation of the work area with physiological saline solution. This saline solution maintains the cutting and abrasion qualities of the tools at an optimum level and gradually removes bone debris and blood. Thus, body 2 of handpiece 1 is provided with a fluid feed pipe 10 at the end thereof that carries tool 6. In the example shown in FIG. 1, pipe 10 is mounted on a ring 12 which is slidably engaged on the nose 14 of handpiece 1. This pipe 10 is connected to a flexible tubing 16 through which the fluid arrives and which is used for directing a jet of fluid towards the operating field. However, the end 18 through which the jet of fluid emerges from pipe 10 cannot be arranged past coupling bushing 4, since this would prevent tool 6 from being easily mounted/removed. Thus, when the tool 6 is long, as is the case of the saw blade shown in FIG. 1, the physiological saline solution outlet point from the pipe 10 is far away from the working area of the tool. Irrigation of the working area is thus not precise and does not always occur in sufficient quantities.

SUMMARY OF THE INVENTION

It is an object of the present invention to overcome this problem by providing both a tool and a device for coupling the tool to a motorised handpiece allowing the operating field to be irrigated precisely and in sufficient quantity.

The present invention thus concerns a coupling device between a surgical instrument drive shaft and a tool shank, characterized in that the coupling device includes a fluid feed element, which is fed from outside the coupling device and which communicates with a channel arranged in the tool shank, said channel emerging at a place on the length of the tool shank.

In a complementary manner, the present invention also concerns a tool for assembly on a surgical instrument drive shaft, said tool having a shank connected to an active element either directly or via a body, characterized in that a channel arranged in the tool shank and, where appropriate, in the body of said tool, emerges at a place on the length of the tool.

Owing to these features, the present invention provides a surgical tool and a device for coupling a tool of this type onto the drive shaft of a surgical instrument, which allow a fluid, such as a physiological saline solution, to be brought as close as possible to the working area of the tool. Indeed, instead of feeding the fluid to the working area by means of an external pipe whose fluid outlet end cannot extend beyond the coupling point between the tool and the handpiece drive shaft, the present invention teaches how to convey the fluid inside the tool and cause it to emerge as close as possible to the active area of said tool. Consequently, it is ensured that the operating field is irrigated precisely and in sufficient quantities to guarantee optimum operating conditions, which is very important, in particular for tools of a certain length.

According to a complementary feature of the invention, the coupling device comprises a support part, which assures the actual connection between the tool shank and the motorised shaft of the surgical instrument, a sleeve on which a bushing is rigidly coupled being arranged concentrically around the support part to define an inlet chamber for the physiological saline solution. The present invention thus provides a coupling device that comprises only three parts, and which is thus both simple to make and extremely compact, this latter aspect greatly facilitating handling of the surgical instrument by the practitioner. Moreover, the set of parts forming the coupling device according to the invention has general rotational symmetry, which removes asperities and other sharp corners which could cause injuries to patients.

According to another feature of the invention, the coupling device allows rigid axial locking between the tool shank and the drive shaft of the surgical instrument owing to a spring loaded ball lock system. As regards rotational locking, this is ensured by a flat portion provided on the tool shank and on which a corresponding flat portion provided on the coupling device abuts. Consequently, the tool is locked both axially and radially during working phases, yet can still be very easily mounted/removed owing to the spring ball lock system. This latter aspect is very important, since it considerably facilitates the task of the practitioner who is required to use several tools during the course of one operation.

BRIEF DESCRIPTION OF THE DRAWINGS

Other features and advantages of the present invention will appear more clearly from the following detailed description of an embodiment of the coupling device according to the invention, this example being given purely by way of non-limiting illustration with reference to the annexed drawing, in which.

DETAILED DESCRIPTION OF THE PREFERRED EMBODIMENTS

The present invention proceeds from the general inventive idea that consists in providing a coupling device and a tool for a motorised surgical instrument which allow in particular precise irrigation of the operating field in sufficient quantities by means of a fluid such as physiological saline solution. The coupling device therefore both allows the tool to be rigidly coupled to the surgical instrument drive shaft and allows a channel extending axially into the tool shank to be placed in communication with an external fluid source. Consequently, the fluid emerges from the tool shank at the active area thereof, i.e. as close as possible to the operating field, which concealed by tissue, is otherwise difficult to access particularly for tools of a certain length. Moreover, the coupling device has a limited number of parts, is compact and free from asperities, which makes the surgical instrument easier to handle. The practitioner becomes less tired and his movements are therefore more precise.

The present invention will now be described with reference to a motorised surgical instrument more particularly intended for operations within the field of rhinoplasty. It goes without saying, however, that the present invention is not limited to this type of operation and that it applies in an identical manner to any type of motorised surgical instrument driving a tool whose working area needs to be irrigated to ensure the best possible performance in terms of cutting, abrasion, drilling or suchlike and the removal of debris and blood.

Figure 1:
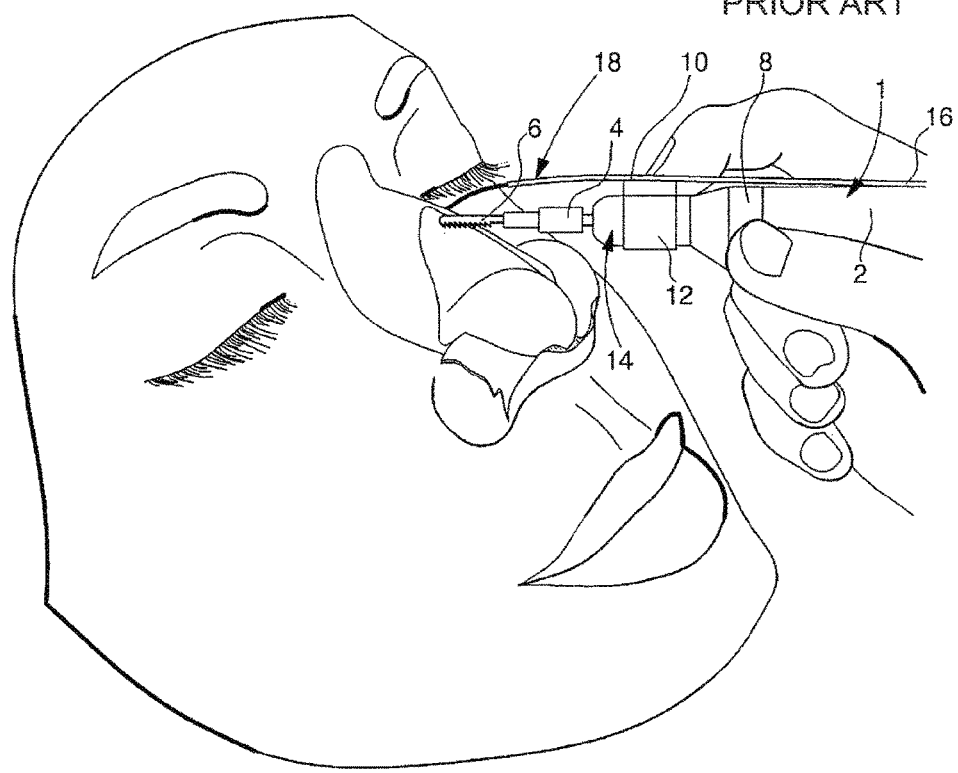
FIG. 1, already cited, is a diagram of a surgical instrument including an operating field irrigation system according to the prior art.
Figure 3:
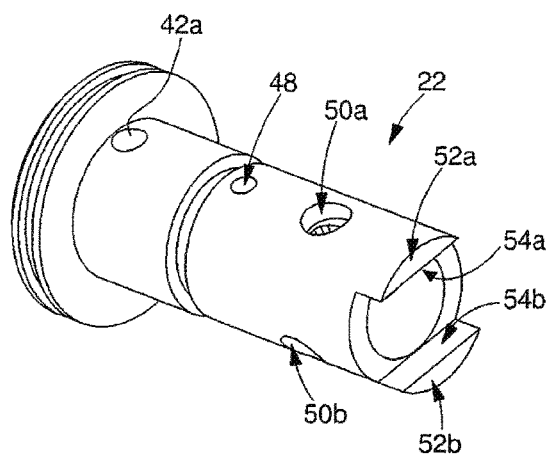
FIG. 3 is a perspective view of the support part.
Figure 2:
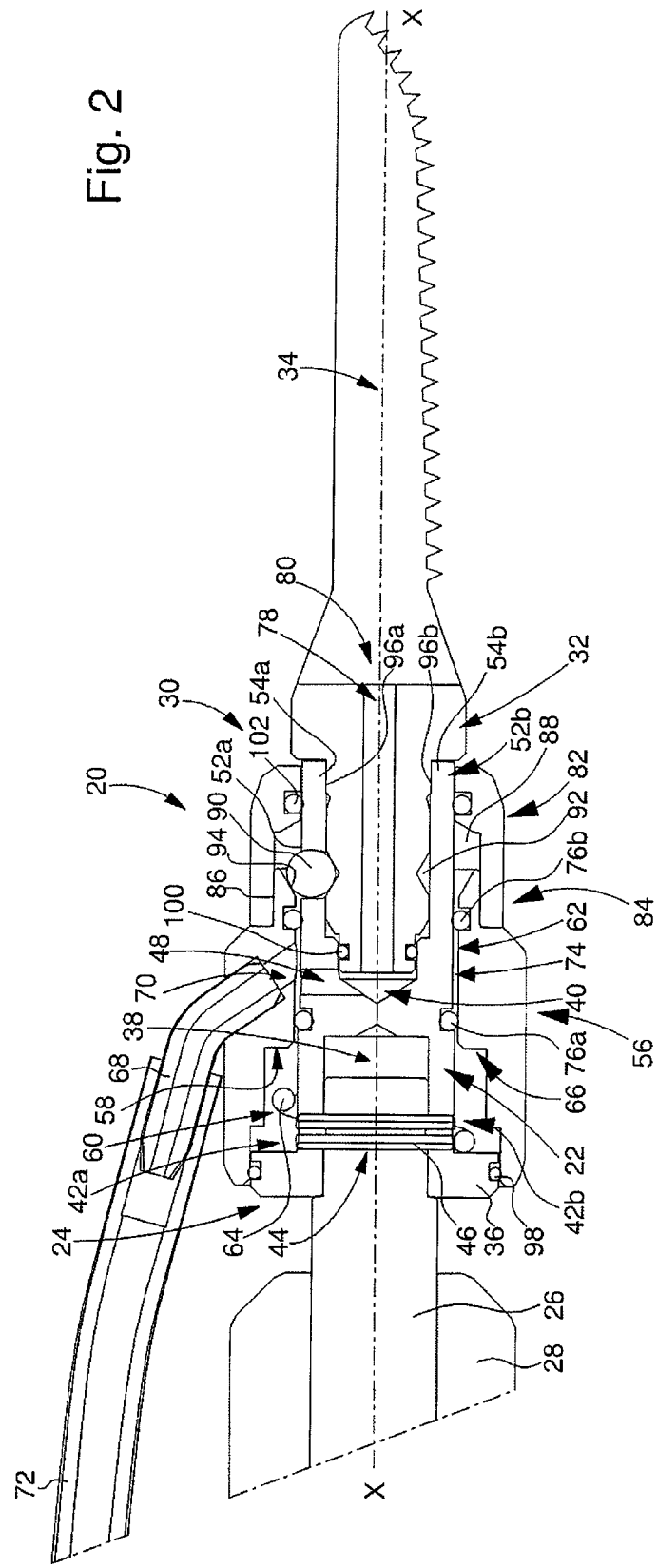
FIG. 2 is a longitudinal cross-section of the coupling device according to the invention in the operating position.

Designated as a whole by the general reference number 20, the coupling device according to the present invention is shown in longitudinal cross-section in its working position in FIG. 2. This coupling device 20 includes first of all a support part 22, which, at a rear or proximal end 24, is carried by a drive shaft 26 of a surgical instrument 28, and which, at a front or distal end 30, carries a shank 32 of a tool 34, in this case a saw. As examination of FIG. 2 reveals, support part 22 is a generally cylindrical part which ends at the rear end 24 in a circular collar or base 36 and in which first and second bores, respectively 38 and 40, are machined. Drive shaft 26 of handpiece 28 is engaged in first bore 38 of support part 22. Preferably, support part 22 is driven and pinned onto drive shaft 26. However, according to a variant, support part 22 could be made integral with drive shaft 26. If it is mounted on drive shaft 26, support part 22 is pierced with two, diametrically opposite holes 42a and 42b, and drive shaft 26 also has a piercing 44. These two holes 42a and 42b and piercing 44 are aligned to allow a pin 46 to pass therethrough. The support part 22 is thus rigidly coupled to drive shaft 26 of surgical instrument 28 while remaining removable for the purposes of maintenance and sterilisation. Shank 32 of tool 34 is engaged in second bore 40 of support part 22. Tool 34 is axially and radially coupled to support part 22 in a way which will be described in detail below. Support part 22 is also pierced with a single hole 48, which forms a pipe, opening out into the second bore 40 as well as with at least one, and preferably three, through holes 50a, 50b and 50c regularly spaced along the perimeter of support part 22 and which also open out into second bore 40. Finally, support part 22 has at the front end 30 thereof, two projecting portions 52a and 52b, diametrically opposite each other, in the arc of a circle and whose opposite surfaces 54a and 54b are flat. The role of these various elements will also be described in detail below.

Secondly, coupling device 20 according to the invention includes a sleeve 56 arranged concentrically around support part 22. This sleeve 56 has a generally cylindrical external shape and an inner space that is also cylindrical with a locally reduced diameter 58. This reduced diameter 58 therefore splits the inner volume of sleeve 56 into a first housing 60, whose diameter is fitted to that of base 36, and a second housing 62, whose diameter is fitted to the external diameter of support part 22. A return spring 64 is arranged inside the first housing 60, abutting, at a rear end, against base 36, and at a front end, against the bottom 66 of said first housing 60. A bent nozzle 68 made of stainless steel is inserted into a first pipe 70, preferably made obliquely relative to the general axis of longitudinal symmetry X-X of coupling device 20. A flexible feed tube 72 for a fluid such as a physiological liquid is connected to bent nozzle 68.

Pipe 70 opens into an annular fluid inlet chamber 74, defined by the gap left free between the wall of the second housing 62 of sleeve 56 and the external surface of support part 22. Annular chamber 74 is sealed by means of two gaskets 76a and 76b placed approximately at the rear end and front end of second housing 62. Annular chamber 74 communicates with the aforementioned pipe 48 which opens into the second bore 40 of support part 22. A sealing gasket 100 must be assembled on the rear end of the shank 32 of the tool 34 to prevent the physiological fluid leaking towards the exterior. Thus, the physiological liquid fed from the exterior via flexible tube 72 and bent nozzle 68 will flow in succession into the first pipe 70, then annular chamber 74 and second pipe 48 before filling the bottom of bore 40. According to the invention, a channel 78 is machined into shank 32 of tool 34 and emerges at a location along the length of shank 32, preferably in active area 80 of tool 34, i.e. if tool 34 is a saw blade, by the teeth of said saw. Thus, the physiological fluid which has run into the bottom of bore 40 will escape by flowing through channel 78 and emerging in active area 80 of tool 34. By forcing the physiological liquid to take a path that leads it from the exterior of coupling device 20 to the centre of shank 32 of tool 34, the point where the physiological fluid emerges can be moved as close as possible to the active part of the tool. The operating field is therefore irrigated precisely and in sufficient quantities to guarantee optimum operating conditions.

We will now consider the locking/unlocking of the tool onto the surgical instrument drive shaft. The coupling device 20 according to the invention includes, thirdly and lastly, a bushing 82 arranged concentrically around support part 22 and rigidly coupled to sleeve 56 preferably by being driven thereon or by another securing technique. For assembly of bushing 82 onto sleeve 56, on the front end side 84 of sleeve 56, there is an annular edge 86 whose external diameter is adapted to the internal diameter of housing 88 defined by bushing 82. As an examination of FIG. 2 reveals, one of the three through holes 50a made in support part 22 and which opens into the second bore 40 is used as a base for a lock ball 90. Lock ball 90 is retained in base 50a, which has, for this purpose, a slightly smaller diameter in the bottom thereof than the largest diameter of ball 90.

Lock ball 90 projects on either side of support part 22, on one side into bore 40 and on the other side into housing 88 defined by bushing 82. More specifically, in the operating position of coupling device 20 as illustrated in FIG. 2, lock ball 90 projects, on the side of second bore 40 into a groove 92 with a V shaped profile made in the external periphery of shank 32 of tool 34 and is held in said groove 92 by sleeve 56, which is forced in the direction of the ball 90 by the elastic return force of spring 64. It can be seen that sleeve 56 abuts against the lock ball 90 via a truncated surface 94 of the annular edge 86 on the inner perimeter thereof. Lock ball 90 thus ensures the axially coupling between tool 34 and drive shaft 26 of surgical instrument 28 via support part 22. Tool 34 is locked in rotation onto drive shaft 26 by the actual support part 22 whose projecting portions 52*a* and 52*b* abut, via their opposite plane surfaces 54*a* and 54*b* on corresponding plane surfaces 96*a* and 96*b* arranged on tool shank 32. In the working position, tool 34 is thus rigidly coupled to drive shaft 26.

Figure 4:
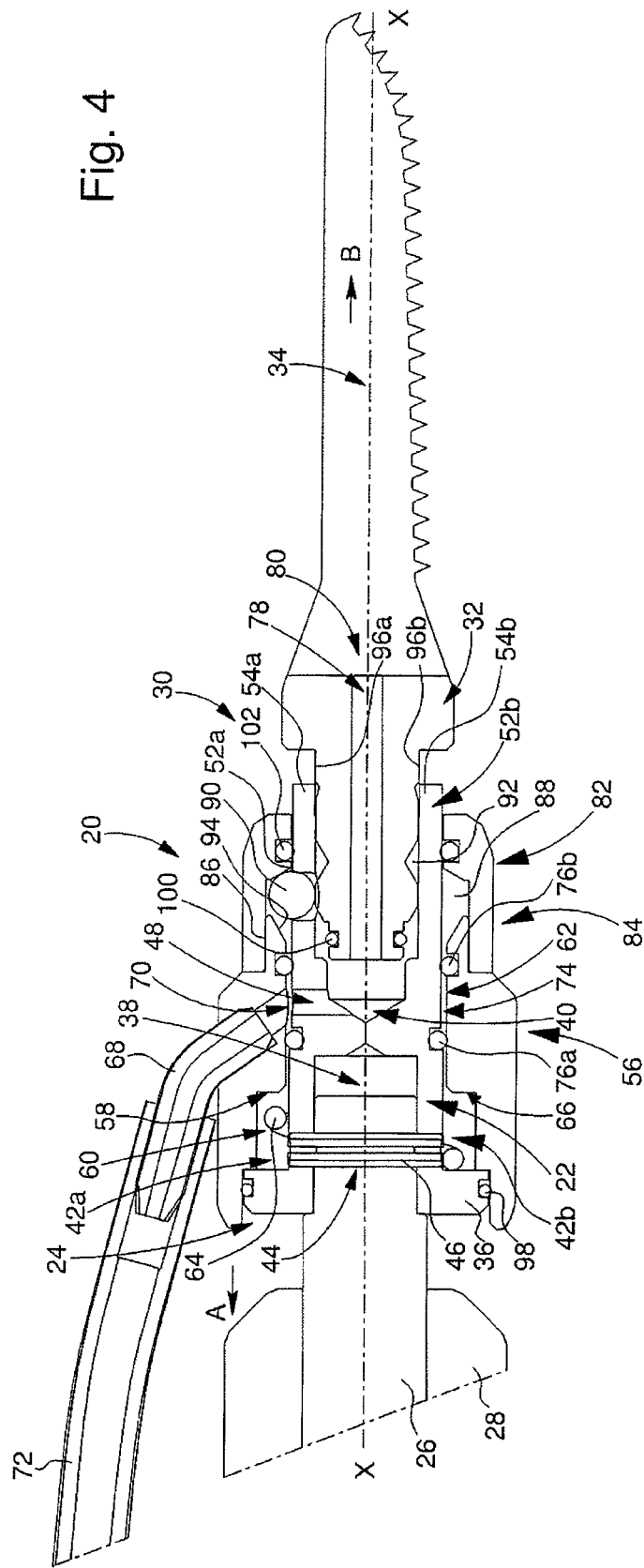
FIG. 4 is a similar view to that of FIG. 2, the coupling device according to the invention being shown in the position where the tool shank is released.

The operation of removing tool 34 will now be examined with reference to FIG. 4. With this aim, the user exerts traction backwards against the return force of spring 64 on the assembly formed by sleeve 56 and bushing 82 (see arrow A). Simultaneously, the user exerts traction forwards on tool 34 (see arrow B). Under the effect of this traction, lock ball 90, which is no longer held in place in groove 92 by truncated surface 94, rolls onto the external perimeter of shank 32 of tool 34 and moves up into housing 88 defined by bushing 82, which is just above ball 90. At that moment, there is no longer any opposition to removal of shank 32 of tool 34. As regards lock ball 90, once shank 32 of tool 34 has been removed from bore 40, it falls back into its base defined by hole 50*a*.

At the rear end of coupling device 20, a sealing gasket 98 can be provided between base 36 and first housing 60. A sealing gasket 102 can also be provided between bushing 82 and support part 22 to prevent any residue from the operation penetrating coupling device 20.

Figure 5:
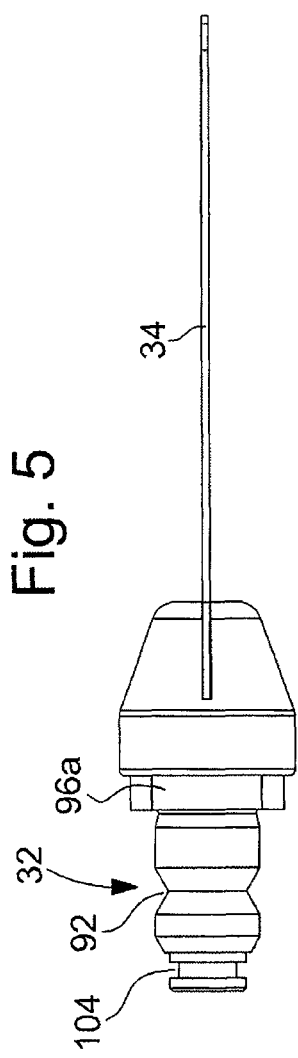
FIG. 5 is a top view of the tool showing the flat surface that allows the tool to be locked radially.

FIG. 5 is a top view of tool 34 showing in particular the flat surface 96*a* on which projecting portion 52*a*, provided at the front end of support part 22, abuts via the corresponding flat surface 54*a* thereof, to lock tool 34 in rotation. FIG. 5 also shows a circular groove 104 which houses sealing gasket 100. V-shaped groove V 92 can also be seen, into which ball 90 projects to lock tool 34 axially.

Figure 6:
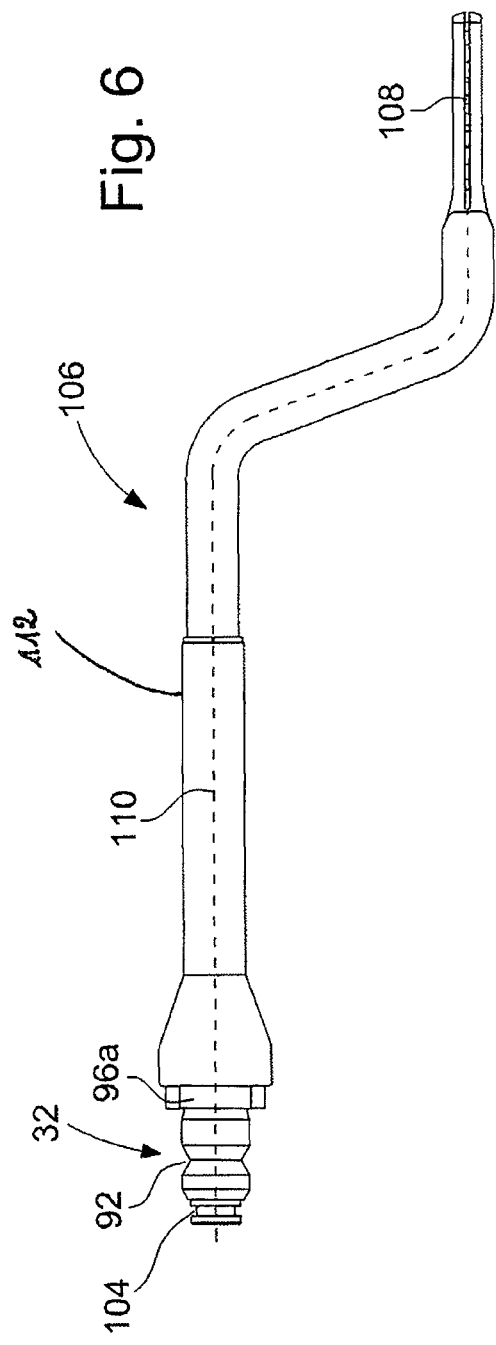
FIG. 6 is a bottom view of a second type of tool according to the invention, said tool including an elongated body, deformed locally into an S shape which extends between the tool shank and the active area thereof and through the entire length of which there runs a channel in which a fluid flows and which emerges in the active area.

FIG. 6 is a bottom view of another type of tool according to the invention. Designated as a whole by the general reference numeral 106, this tool differs from that shown in FIGS. 2, 4 and 5 only in that the shank 32 thereof, which is used to assemble the tool to the surgical instrument drive shaft via support part 22 according to the invention, is connected to the active part 108 thereof, in this case a semi-circular saw blade, via an elongated body 112. According to the invention, a channel 110 (shown in dotted lines in FIG. 6) extends through tool 106, said channel 110 being machined in shank 32 and into body 112 of tool 106 and emerging at a location along the length of said body of tool 106, preferably in proximity to the active are 108 thereof. After machining channel 110 in shank 32 and body 112 of tool 106, tool 106 may be given the desired shape, for example it may be partially S shaped as shown in the drawing. It is clear that, thanks to the present invention, physiological liquid can be made to emerge as close as possible to the active area of the tool according to the invention, even when the latter is of significant length.

What is claimed is:

1. An assembly comprising:
    a surgical instrument including an operating field irrigation system, said surgical instrument comprising a handpiece and a drive shaft, wherein a portion of said drive shaft is arranged inside said handpiece and an end of the drive shaft extends outside the handpiece of the surgical instrument, and wherein the drive shaft is configured to move in a reciprocal motion by a drive;
    a surgical tool comprising a shank and having a channel arranged in the shank of the surgical tool and wherein said channel starts at a first end of said shank and emerges at a location along a length of the surgical tool;
    a coupling device configured to lock the drive shaft and the shank of the surgical tool together, both axially and radially, in a manner that the shank of the surgical tool and the end of the drive shaft do not make direct contact and the coupling device transmits the reciprocal motion of the drive shaft to the surgical tool, wherein the coupling device has a first end surrounding the end of the drive shaft, said coupling device has a second end mounted on the shank of the surgical tool at the first end of said shank; and
    a pipe extending outside of said coupling device;
    wherein the coupling device is further configured to unlock from the drive shaft and the surgical tool, wherein said first and second ends of the coupling device are removable from the end of the drive shaft and from the first end of the shank of the surgical tool respectively;
    wherein the coupling device includes an internal fluid feed pathway communicating with an exterior surface of the coupling device,
    wherein the coupling device defines an entry hole for the fluid feed pathway on the exterior surface of the coupling device, said entry hole is arranged at a point separate from the surgical instrument, wherein the pipe is arranged and connected to the entry hole outside the coupling device, wherein said fluid feed pathway travels through a portion of the coupling device, and
    wherein the fluid feed pathway communicates with the channel arranged in the shank of the surgical tool in a manner that leads fluid from the pipe, through the exterior of the coupling device, through the shank of the surgical tool and the length of the surgical tool.

2. The assembly according to claim 1, wherein the channel arranged in the surgical tool passes through the entire shank and through part of the surgical tool.

3. The assembly according to claim 2, wherein the coupling device further includes a support part that, at a first end of the support part, is rigidly coupled to the drive shaft of the surgical instrument, wherein said support part is removable from the drive shaft, wherein the support part carries the shank of the surgical tool at a second end of the support part.

4. The assembly according to claim 3, wherein the support part is driven and pinned onto the drive shaft of the surgical instrument, and wherein said support part is removable from the drive shaft.

5. The assembly according to claim 3, wherein, at the first end of the support part, the support part has a bore that communicates with the fluid feed pathway, and wherein the shank of the surgical tool is engaged in the bore.

6. The assembly according to claim 4, wherein, at the first end of the support part, the support part has a bore that communicates with the fluid feed pathway and the shank of the surgical tool is engaged in the bore.

7. The assembly according to claim 3, wherein the coupling device further includes a sleeve surrounding the support part, wherein the sleeve delimits, with the support part, an annular fluid inlet chamber.

8. The assembly according to claim 7, wherein the annular fluid inlet chamber is sealed at a first end and at a second end by two first sealing gaskets and wherein a second sealing gasket is mounted on the first end of the surgical tool shank.

9. The assembly according to claim 7, wherein the coupling device further includes a bushing surrounding the support part and rigidly coupled to the sleeve, and wherein the sleeve and the bushing reversibly locks the surgical tool shank axially on the support part.

10. The assembly according to claim 8, wherein the coupling device further includes a bushing surrounding the support part and rigidly coupled to the sleeve, and wherein the sleeve and the bushing reversibly locks the tool shank axially on the support part.

11. The assembly according to claim 9, wherein the sleeve and the bushing is returned axially to a surgical tool locking position on the support part by a return spring, and wherein a lock ball housed in a base made in the support part is forced by the sleeve into a groove arranged on a periphery of the shank of the surgical tool.

12. The assembly according to claim 10, wherein the sleeve and the bushing is returned axially to a surgical tool locking position on the support part by a return spring, and wherein a lock ball housed in a base made in the support part is forced by the sleeve into a groove arranged on a periphery of the shank of the surgical tool.

13. The assembly according to claim 9, wherein, in a releasing position, the sleeve and the bushing is brought into position for releasing the surgical tool shank against a return force of a return spring, a lock ball being located by an inner housing, delimited by the bushing, and wherein a diameter of the housing is enables the lock ball to exit the groove arranged on the periphery of the shank of the surgical tool.

14. The assembly according to claim 11, wherein, in a releasing position, the sleeve and the bushing is brought into position for releasing the surgical tool shank against a return force of the return spring, the lock ball is located by an inner housing, delimited by the bushing, and wherein a diameter of the housing enables the lock ball to exit the groove arranged on the periphery of the shank of the surgical tool.

15. The assembly according to claim 12, wherein, in a releasing position, the sleeve and the bushing is brought into position for releasing the surgical tool shank against a return force of the return spring, the lock ball is located by an inner housing, delimited by the bushing, and wherein a diameter of the housing enables the lock ball to exit the groove arranged on the periphery of the shank of the surgical tool.

16. The assembly according to claim 9, wherein a return spring abuts, at a first end, against a base provided on the support part and against an inner shoulder provided in the sleeve at a second end.

17. The assembly according to claim 13, wherein the return spring abuts, at a first end, against a base provided on the support part and against an inner shoulder provided in the sleeve at a second end.

18. The assembly according to claim 3, wherein, for radial immobilization, the surgical tool shank has a flat surface on which abuts a corresponding flat surface at a second end of the support part.

19. An assembly according to claim 1
wherein the fluid feed pathway communicates with a channel arranged in the shank of the surgical tool, and
wherein the coupling device further includes a sleeve surrounding a support part which, at a first end, ends in a base which is rigidly coupled to the drive shaft of the surgical instrument and which, at a second end, carries the first end of the shank of the surgical tool, wherein the sleeve delimits, with the support part, an inner space with a locally reduced diameter which splits the inner space into a first housing, whose diameter is fitted to that of the base of the support part, and a second housing whose diameter is fitted to the external diameter of the support part.

* * * * *